US009539023B2

(12) United States Patent
Marotte (10) Patent No.: US 9,539,023 B2
(45) Date of Patent: Jan. 10, 2017

(54) CIRCUMCISION TOOL

(76) Inventor: Jeffrey Marotte, Conway, AR (US)

(*) Notice: Subject to any disclaimer, the term of this patent is extended or adjusted under 35 U.S.C. 154(b) by 533 days.

(21) Appl. No.: 13/474,379

(22) Filed: May 17, 2012

(65) Prior Publication Data
US 2013/0310844 A1 Nov. 21, 2013

(51) Int. Cl.
| *A61B 17/326* | (2006.01) |
| *A61B 17/064* | (2006.01) |
| *A61B 17/072* | (2006.01) |
| *A61B 17/00* | (2006.01) |
| *A61B 17/115* | (2006.01) |

(52) U.S. Cl.
CPC ......... *A61B 17/326* (2013.01); *A61B 17/0643* (2013.01); *A61B 17/072* (2013.01); *A61B 2017/00004* (2013.01); *A61B 2017/07221* (2013.01); *A61B 2017/1157* (2013.01)

(58) Field of Classification Search
CPC ... A61B 17/326; A61B 17/115; A61B 17/282; A61B 17/1155; A61B 2017/07221; A61B 2017/1225; A61B 2017/07285; A61B 2017/32004; A61B 2017/00004; A61B 2017/1157; A61B 17/068; A61B 17/285; A61B 17/295; A61B 17/072; A61B 17/0643
USPC ............ 606/118, 139, 219; 227/175.1, 180.1
See application file for complete search history.

(56) References Cited

U.S. PATENT DOCUMENTS

| 2,076,468 A | 4/1937 | LaBreck |
| D119,180 S | 2/1940 | Goldstein |
| 2,353,647 A | 7/1944 | Carmichael |
| 2,376,893 A | 5/1945 | Baker |
| 2,533,373 A | 12/1950 | Hinckley et al. |
| 2,646,047 A | 7/1953 | Bronstein |
| 2,688,969 A | 9/1954 | Livoti |
| 3,490,675 A | 1/1970 | Green et al. |
| 3,566,873 A | 3/1971 | Melges |
| 3,612,057 A | 10/1971 | Freedman |
| 3,741,215 A | 6/1973 | Ayad |
| 4,428,376 A | 1/1984 | Mericle |

(Continued)

FOREIGN PATENT DOCUMENTS

| DE | 19851792 | 6/2000 |
| GB | 1379374 | 1/1975 |

(Continued)

*Primary Examiner* — Julian W Woo
*Assistant Examiner* — Lucas Paez
(74) *Attorney, Agent, or Firm* — Kenneth H. Jack; Davis & Jack, L.L.C.

(57) ABSTRACT

A circumcision tool having an outer jaw having front, rear, and medial blade passage channels; front and rear pluralities of skin fasteners; outer front and outer rear staple inserts releasably holding the front and rear pluralities of skin fasteners within the front and rear blade passage channels; front, rear, and medial blades, the medial blade having a cutting edge; slide tracks connecting the front, rear, and medial blades to the outer jaw; a cam connected operatively to the front, rear, and medial blades, for inwardly moving the front, rear, and medial blades toward the front, rear, and medial blade passage channels in alignments with the front and rear pluralities of skin fasteners, and in alignment of the medial blade with the medial blade passage channel; an inner jaw; and a vice grips actuator connected to the inner and outer jaws for alternatively retracting and splaying the inner and outer jaws.

17 Claims, 12 Drawing Sheets

(56) References Cited

U.S. PATENT DOCUMENTS

| | | |
|---|---|---|
| 4,491,136 A | 1/1985 | LeVeen |
| 5,163,943 A | 11/1992 | Mohiuddin et al. |
| 5,439,466 A | 8/1995 | Kilejian |
| 5,653,373 A * | 8/1997 | Green et al. ............... 227/175.1 |
| 5,860,988 A | 1/1999 | Rawlings |
| 6,660,012 B2 | 12/2003 | Lahiji |
| 7,591,824 B2 | 9/2009 | Dave |
| 7,857,185 B2 * | 12/2010 | Swayze et al. ............. 227/175.2 |
| 7,988,028 B2 * | 8/2011 | Farascioni et al. ........ 227/180.1 |
| 2004/0215210 A1 | 10/2004 | Duel |
| 2006/0219753 A1 | 10/2006 | Chiu et al. |
| 2007/0244516 A1 | 10/2007 | Chiu et al. |
| 2008/0021482 A1 | 1/2008 | Tomlinson |
| 2010/0114112 A1 | 5/2010 | Mansour |
| 2011/0253766 A1 * | 10/2011 | Baxter et al. ............... 227/176.1 |

FOREIGN PATENT DOCUMENTS

| | | |
|---|---|---|
| JP | 04051945 | 2/1992 |
| JP | 2011147771 | 8/2014 |
| WO | WO2005099598 | 10/2005 |
| WO | WO2009114529 | 9/2009 |

\* cited by examiner

CIRCUMCISION TOOL

FIELD OF THE INVENTION

This invention relates to medical tools and implements which specially adapted for assisting in the performance of male penile circumcisions operations.

BACKGROUND OF THE INVENTION

Where an adult male's penile foreskin is in its prepuce configuration as a glans protecting membrane (with the foreskin's mucocutaneous zone or layer annularly underlying the foreskin's outer skin layer), an annulus is formed and defined, such annulus normally being flexibly closed and being outwardly expandable. The inner periphery of such annulus comprises the outer periphery of the male's penile glans. Since the skin defining the outer periphery of such annulus is mucocutaneous, the environment within such annulus is typically warm and moist, and often undesirably promotes growth and reproduction of colonies of bacterial pathogens such as *Neisseria gonorrhoeae* and *Treponema pallidum* or viral pathogens such as human immune deficiency virus and human papillomavirus. Such pathogens tend to be undesirably transmitted to other persons via sexual contact or such pathogens may directly infect the host through tears within the foreskin.

The male's penile foreskin is commonly known to be surgically excised or amputated. Reasons for performing male foreskin circumcision operations are numerous, including social and religious practices, attempts to lessen risks of transmission of pathogens to sexual partners, and relatively medically necessary excisions of foreskins which are in fact infected with HIV. In a known mode of performing a surgical circumcision operation, a circumferentially extending incision or circumcising cut is extended about the male's penile foreskin, such incision passing completely through both the foreskin's outer skin and underlying mucocutaneous layers to form a pair of incised skin edges. In the event such incised skin edges are held in close proximity with each other during healing, the skin sections naturally graft to each other to form a renewed and integral outer skin surface which lacks the excised or amputated foreskin layers, and which no longer forms an annulus about the glans. In order to effectively hold such incised skin edges in close proximity during healing, skin staples or stitches are commonly used.

Utilizing a scalpel for making a circumcising incision, followed by closing the incision through use of skin staples or stitches is typically mechanically cumbersome and complex, and is typically complicated by continuous hemorrhaging during placement of stitching or staples along the incision. From and after the identification of the HIV virus in 1981, such known procedures for surgical circumcisions have been viewed as posing a heightened risk to the surgeon. Direct tactile manipulations of surgical tools such as scalpels, needles, and sutures have always been accompanied by a risk of cutting or piercing the surgeon's fingers, resulting in transmission of a patient's blood bourne pathogens to the surgeon. Where the pathogen is HIV which directly resides within a foreskin being excised, the heightened risk to the surgeon includes a prospect of being afflicted with AIDS which has a high fatality rate. The instant inventive tool performs all skin cutting and skin piercing steps at a tool front end, and allows the surgeon's hands and fingers to reside at the tool's rearward end during the skin cutting and skin piercing steps. Thus, the tool, in addition to simplifying the circumcision procedure and reducing hemorrhaging, advantageously acts as a buffer against transmissions of blood bourne pathogens from the patient to the surgeon by allowing the surgeon's hands and fingers to remain removed from skin cutting and piercing structures.

Accordingly, the instant inventive circumcision tool solves or ameliorates the problems, difficulties, and deficiencies discussed above, by providing tool structures for automatically stapling the male's foreskin along parallel circumferential lines to create a hemorrhage free circumferential incision zone, and by automatically and substantially simultaneously circumferentially incising the foreskin within such zone.

BRIEF SUMMARY OF THE INVENTION

A first structural component of the instant inventive circumcision tool comprises an outer jaw having front, rear, and medial blade passage channels. In a preferred embodiment, the outer jaw element is longitudinally oblongated along a front to rear dimension, and the outer jaw has a concave inner face. Also, in the preferred embodiment, the curvature of the outer jaw's concave inner face substantially matches the convex curvature of a male's penile foreskin. The front, rear, and medial blade passage channels are preferably positioned at the frontward end of the outer jaw, and such channels are preferably arranged so that they arcuately extend laterally across the width of the outer jaw. In the preferred embodiment, the outer jaw (along with all other major structural components of the circumcision tool) comprises durable and rigid plastic. Suitably, the outer jaw may alternatively comprise stainless steel.

Further structural components of the instant inventive circumcision tool comprise front and rear pluralities of skin fasteners. While the skin fasteners may comprise single legged fastening posts or nails, the skin fasteners are preferably configured as staples. In a preferred embodiment, the skin fasteners are composed of plastic, and preferably a bio-absorbable polymer. Suitably, the skin fasteners may alternatively comprise maleable and bendable metal legs which upon insertion may be crimped together as means for stopping staple extractions.

Further structural components of the instant inventive circumcision tool comprise outer front and outer rear fastener retaining means which are adapted for respectively releasably holding the front and rear pluralities of skin fasteners at or in alignments with the outer jaw's front and rear blade passage channels. In a preferred embodiment, the outer front and outer rear fastener retaining means comprise curved plastic inserts which are specially fitted for nesting receipts by and retentions within the front and rear blade passage channels. Such inserts are preferably slotted in a manner allowing the skin fasteners to be received and temporarily held within the slots. Such slots are also preferably positioned and sized for outward to inward through passages of staple driving structures which are further described below.

Further structural components of the instant inventive circumcision tool comprise front, rear, and medial blades, the medial blade having an inner skin cutting edge, and the front and rear blades having multiple inner staple driving lands or faces.

Further structural components of the instant inventive circumcision tool comprise moveable mounting means which operatively connect the front, rear, and medial blades with respect to the outer jaw's front, rear, and medial blade passage channels. In a preferred embodiment, the movable mounting means comprise a rigid plate to which the front, rear, and medial blades are rigidly attached, and from which such blades inwardly extend. The movable mounting means preferably further comprise a slide tracks and slide pins combination, such combination's slide tracks being rigidly mounted in relation to the outer jaw, and such combination's slide pins being rigidly mounted in relation to the plate. Relative orientations of such movable mounting means' slide tracks and slide pins facilitate reciprocating inward and outward movements of the blades into and out of the outer jaw's front rear and medial blade passage channels. Other commonly known mechanical means for facilitating such reciprocating motion of the blades with respect to the outer jaw, such as slide slot assemblies, pivot arm assemblies, and living hinge assemblies, are considered to fall within the scope of the invention.

Further structural components of the instant inventive circumcision tool comprise blade and fastener driving means which are connected operatively to the front, rear, and medial blades. In a preferred embodiment, such driving means comprise a rotatable cam whose eccentric end is positioned for inwardly driving impingement against an outer surface of the plate. In a preferred embodiment, rotation of the driving means' cam is facilitated by an axle which may advantageously have a rearward extension which terminates at a manually turnable knob. Other commonly known mechanical means for inwardly driving the blade and fastener components of the instant inventive circumcision tool, such as screw actuators, lever actuators, spring driven actuators, and manually depressible button actuators, are considered to fall within the scope of the invention.

A further structural component of the instant inventive circumcision tool comprises an inner jaw which, like the outer jaw, is longitudinally oblongated. The inner jaw preferably has a convex outer face whose curvature substantially matches the curvature of the outer jaw's concave inner face. The forward end of inner jaw is preferably specially fitted and curved so that it may be easily be inserted into and may reside within the annulus existing between the male's penile foreskin and glans.

Further structural components of the instant inventive circumcision tool comprise clamping means which are connected operatively to the inner and outer jaws, the clamping means being adapted for alternatively retracting and splaying the inner and outer jaws. In a preferred embodiment, the clamping means comprise a vice-grips actuator (alternatively known as locking pliers or a mole grip actuator), such preferred clamping means allowing a medical practitioner operating the tool to manually squeeze inner and outer hand grip components of the actuator to retract and hold the tool's inner and outer jaws at a selected calibrated displacement, such displacement preferably being slightly less than the combined thicknesses of the outer skin and mucocutaneous layers of the male's penile foreskin. Such preset jaw retraction limit advantageously facilitates secure holding of the male's foreskin without skin crushing. While a vice grips assembly constitutes a preferred clamping means, other clamping means such as jack screw assemblies, common "X" pivoting pliers assemblies, and independently movable attachable and detachable jaws assemblies, may be suitably alternatively utilized, and are considered to fall within the scope of the invention.

In use of the instant inventive circumcision tool (and assuming provisions of preferred components as described above), curved plastic fastener retainers containing front and rear arrays of staples may initially be inserted into the outer jaw's front and rear blade passage channels. Thereafter, the forward end of the tool's inner jaw may be inserted into the male's foreskin opening via expansion of the foreskin's frenar band, such extension causing the forward end of the lower jaw to reside within the annulus between the foreskin and the glans. Thereafter, the medical practitioner may manually squeeze the inner and outer hand grips of the preferably provided vice grip clamping means toward each other until such actuator's over-center lock effectively retracts and holds the tool's inner and outer jaws at a preset, and preferably precisely calibrated, foreskin compressing displacement. Thereafter, and assuming that the tool's preferred cam actuated driving means are turn knob actuated, the practitioner may manually turn such knob, causing the eccentric end of the cam to inwardly drive the tool's rear, medial and front blades.

Upon the cam motion, the blades impinge against and inwardly drive the front and rear pluralities of skin fasteners while simultaneously driving the cutting blade inwardly for incising the foreskin. Extension of the skin fasteners through the outer skin and mucocutaneous layers of the foreskin simultaneously fastens those foreskin layers together both in front of and to the rear of the incision. Such foreskin fastening defines a bloodless incision zone which advantageously reduces hemorrhaging from the incision which extends along the zone.

Where the front and rear pluralities of skin fasteners comprise staples, and where such staples are formed of maleable metal, the outer face of the inner jaw may suitably be configured for crimping the staple legs together, such staple legs' crimps constituting suitable staple extraction stopping means. However, the extraction stopping means which are preferably provided comprise front and rear pluralities of female staples whose outwardly opening sockets are specially fitted and positioned for receiving the inner ends of the overlying "male" staples.

Where front and rear pluralities of female staples are provided as staple extraction stopping means, inner front and inner rear insert receiving channels which are similar to the outer jaw's insert receiving channels, are preferably provided within the outer face of the lower jaw. The inner jaw's inserts preferably receive and hold the female staple extraction steps in a manner similar to the outer inserts' retentions of the outwardly overlying male staples. Like the male staples, such female staples are preferably composed of bio-absorbable material.

In a preferred embodiment of the circumcision tool, the inner and outer faces of the outer and inner jaws span 60° of arc. Such curvature allowing each staple deployment and incision to complete ⅙ of a circumcision while simultaneously staunching blood flow at the incision site. Where such circumcision tool geometry is provided, six substantially identical renditions of the tool may be provided, each being preloaded with inner and outer staple inserts, and each being utilized in quick succession for a complete and substantially bloodless circumcision.

Accordingly, objects of the instant invention include the provision of a circumcision tool which incorporates structures, as described above, which arranges those structures in relation to each other, as described above, and which utilizes those structures in accordance with the steps described above for the achievement of the beneficial functions, as described above.

Other and further objects, benefits, and advantages of the present invention will become known to those skilled in the art upon review of the Detailed Description which follows, and upon review of the appended drawings.

DETAILED DESCRIPTION OF A PREFERRED EMBODIMENT

Figure 1:
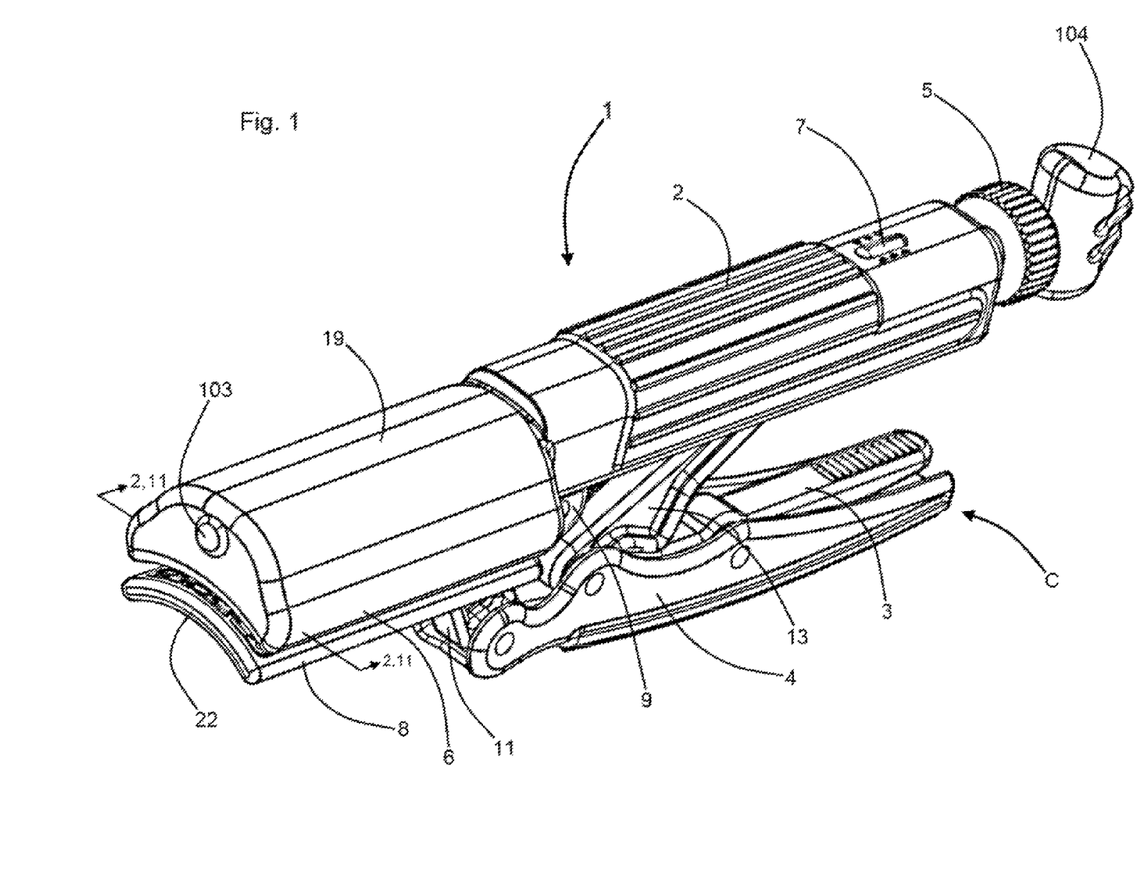
FIG. 1 is a perspective view of a preferred embodiment of the instant inventive circumcision tool.
Figure 2:
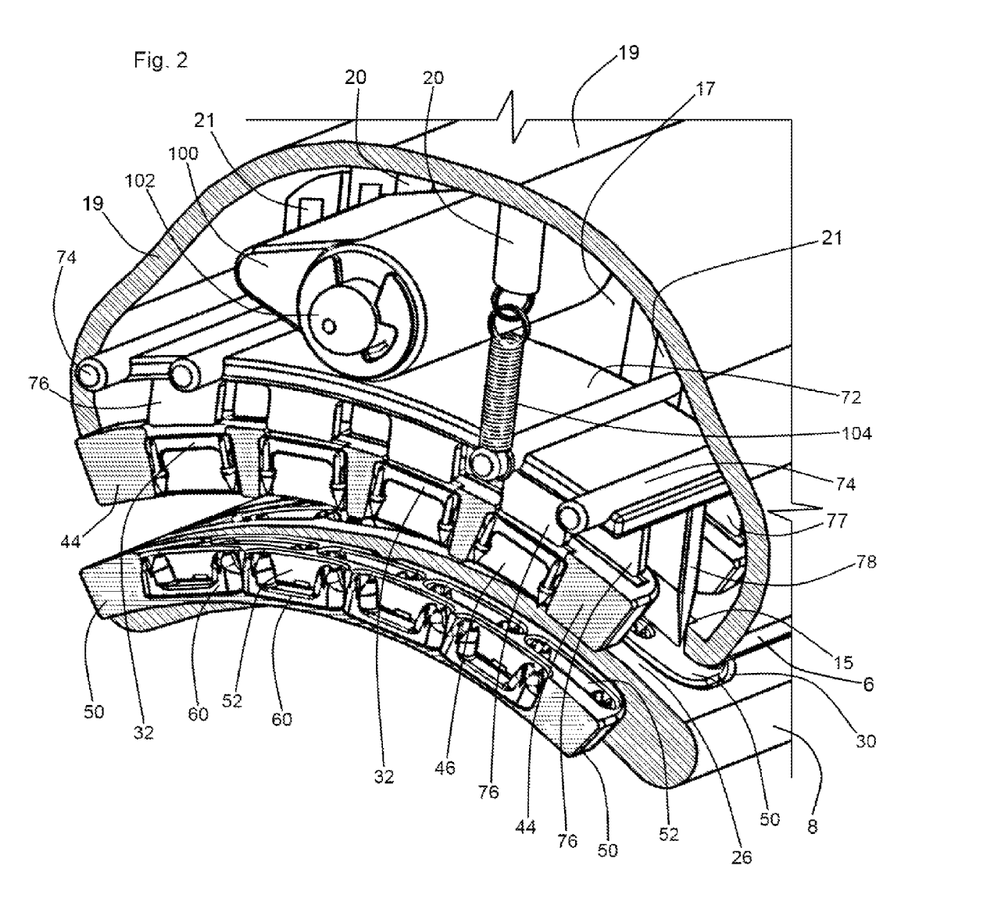
FIG. 2 is a partial sectional view, as indicated in FIG. 1.
Figure 3:
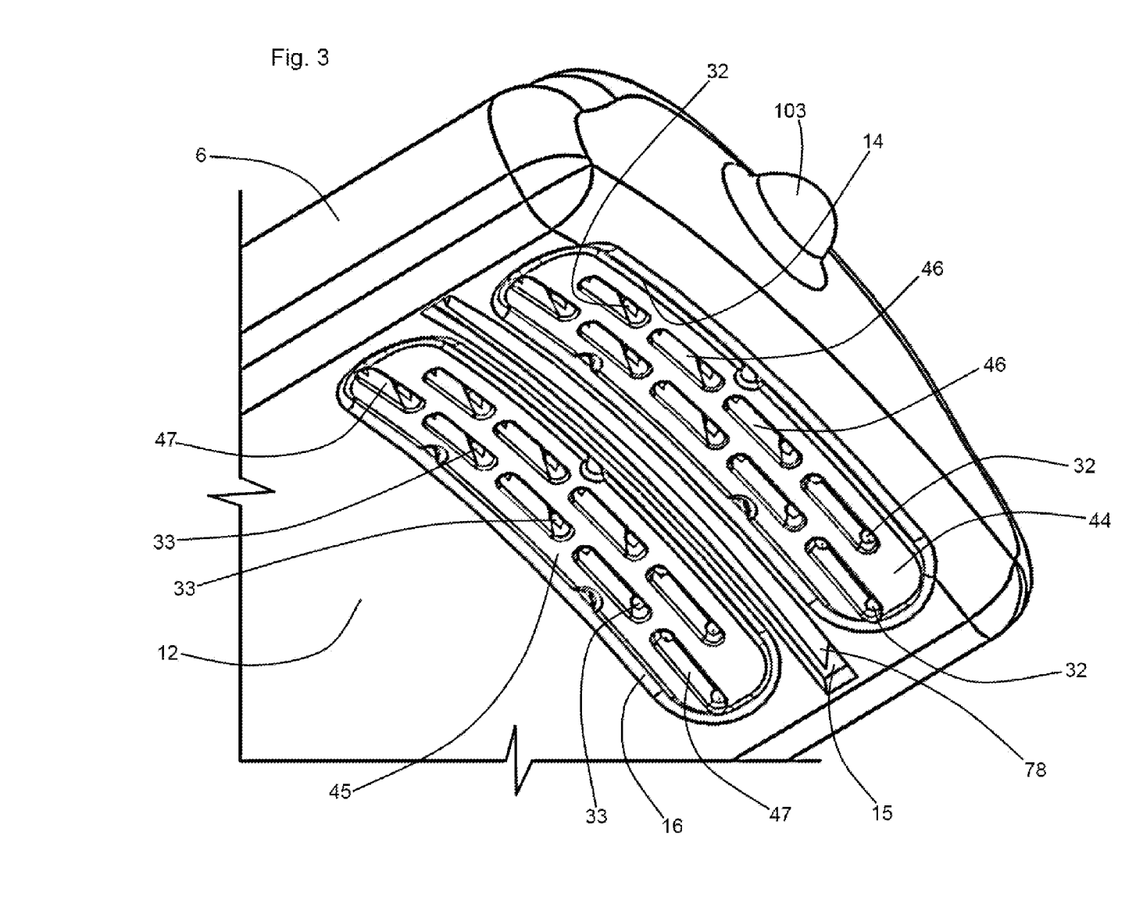
FIG. 3 is a partial view of a forward end of an upper jaw element of the structure depicted in FIG. 1.

Referring now to the drawings, and in particular to Drawing FIGS. 1-3, a preferred embodiment of the instant inventive circumcision tool is referred to generally by Reference Arrow 1. The circumcision tool 1 comprises an outer jaw 6 which extends longitudinally or along a front to rear orienting line, the outer jaw 6 having a curved lateral extension. The outer jaw 6 has a convex inner face 12, and the front end of the outer jaw 6 preferably includes front 14, rear 16, and medial 15 blade passage channels, each such channel preferably opening both outwardly and inwardly.

Figure 5:
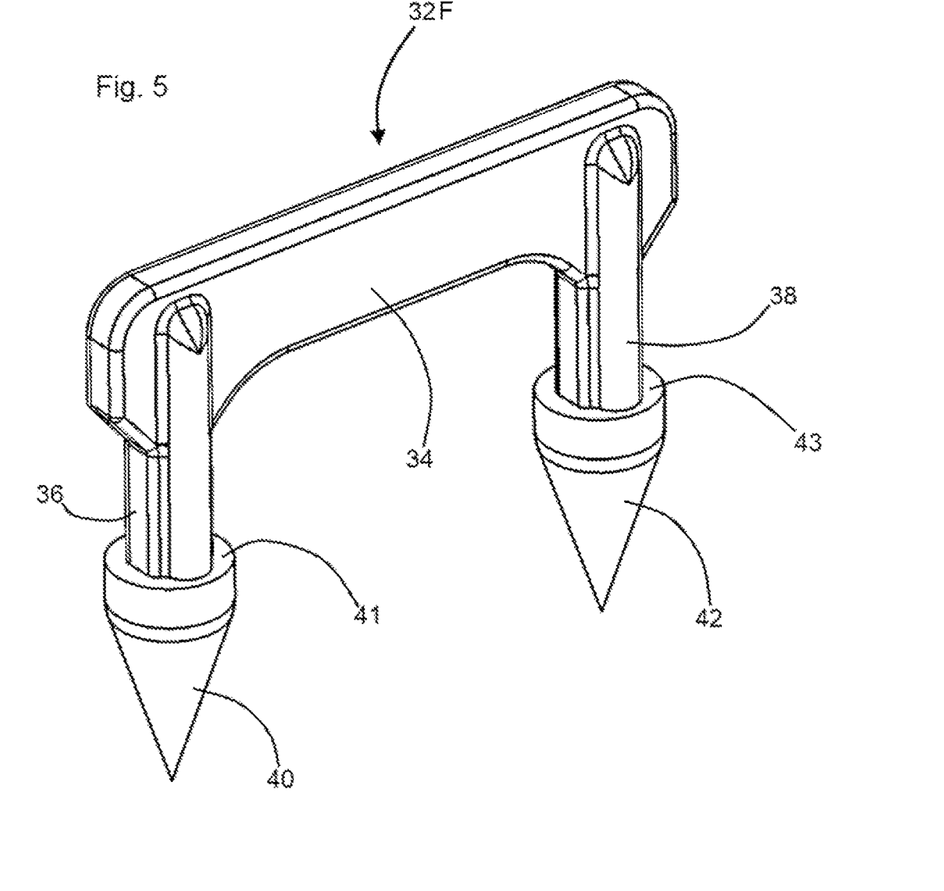
FIG. 5 is a perspective view of a male staple component of the instant invention.

Referring to FIG. 3, front and rear pluralities of skin fasteners 32 and 33 respectively reside within blade passage channels 14 and 16. Referring further simultaneously to FIG. 5, each skin fastener among the front and rear pluralities of skin fasteners 32 and 33 is preferably configured substantially identically with the front skin fastener which is identified in FIG. 5 by Reference Arrow 32F. Such skin fastener 32F preferably has an outer crown 34, left and right inwardly extending legs 36 and 38, and left and right skin piercing ends 40 and 42 at the inner ends of legs 36 and 38. The fastener 32F also preferably comprises outwardly facing extraction stop engaging ridges 41 and 43 which function as stop attaching means. The fastener 32F depicted in FIG. 5 constitutes a "male" staple fastener, and each of the outwardly mounted skin fasteners among the front and rear pluralities of skin fasteners 32,33 depicted in FIG. 3 is preferably configured substantially identically with the fastener 32F depicted in FIG. 5. In a preferred embodiment, each of the fasteners 32,33 is composed of a bioabsorbable polymer. Fastener 32F and each fastener 32,33 are intended as being representative of other common fastener types such as crimpable maleable metal fasteners, and nail or post fasteners.

Figure 4:
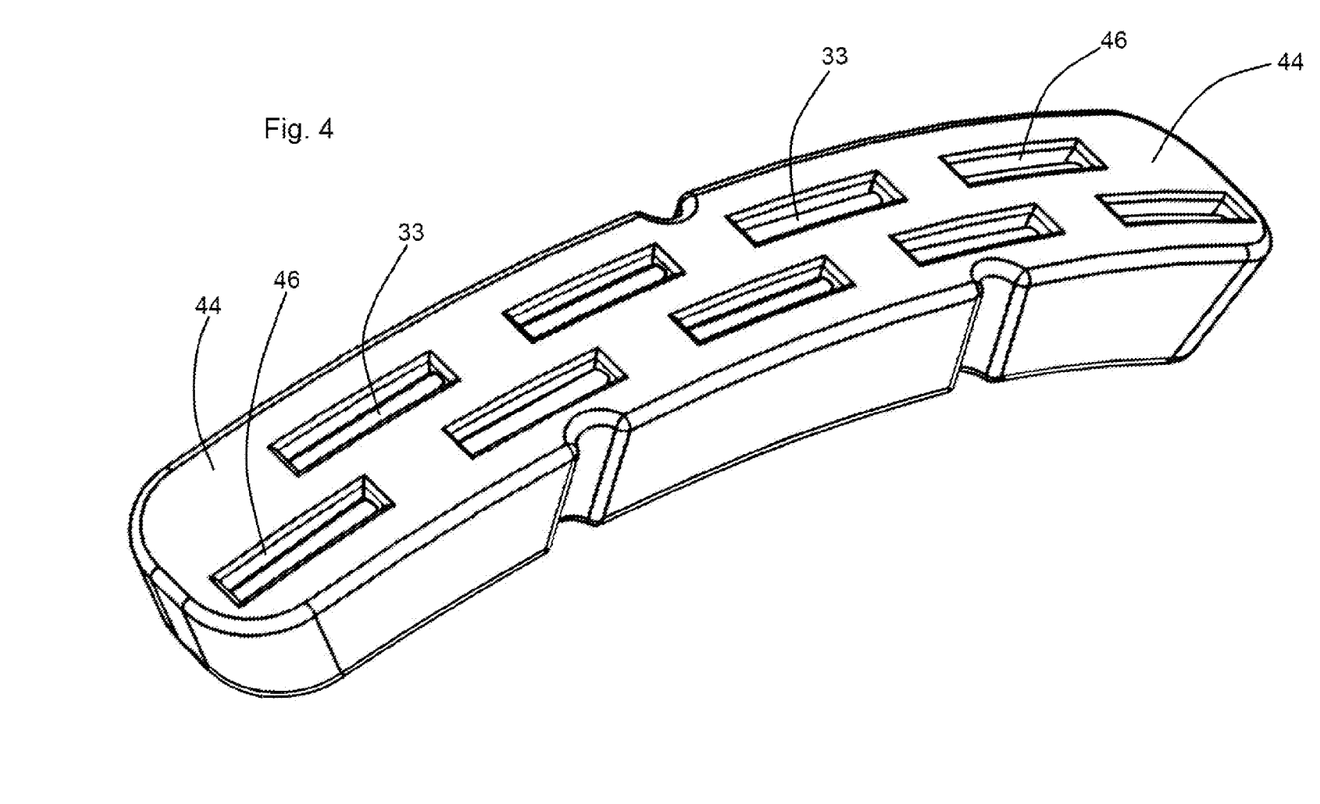
FIG. 4 is a perspective view of a front outer insert component of the instant invention.

Referring simultaneously to FIGS. 3-5, means for retaining the front and rear pluralities of skin fasteners 32 and 33 within the front and rear blade passage channels 14 and 16 are preferably provided. In a preferred embodiment, such retaining means comprise outer front and outer rear inserts 44 and 45, such inserts being respectively closely fitted for nesting receipts within blade passage channels 14 and 16. Slot pluralities 46 and 47 respectively extend through inserts 44 and 45, such slots 46 and 47 dually functioning for temporarily receiving and holding the pluralities of fasteners 32 and 33, and for guiding such fasteners as they are inwardly driven (as further discussed below) for piercing impingements against a male's penile foreskin.

Figure 10:
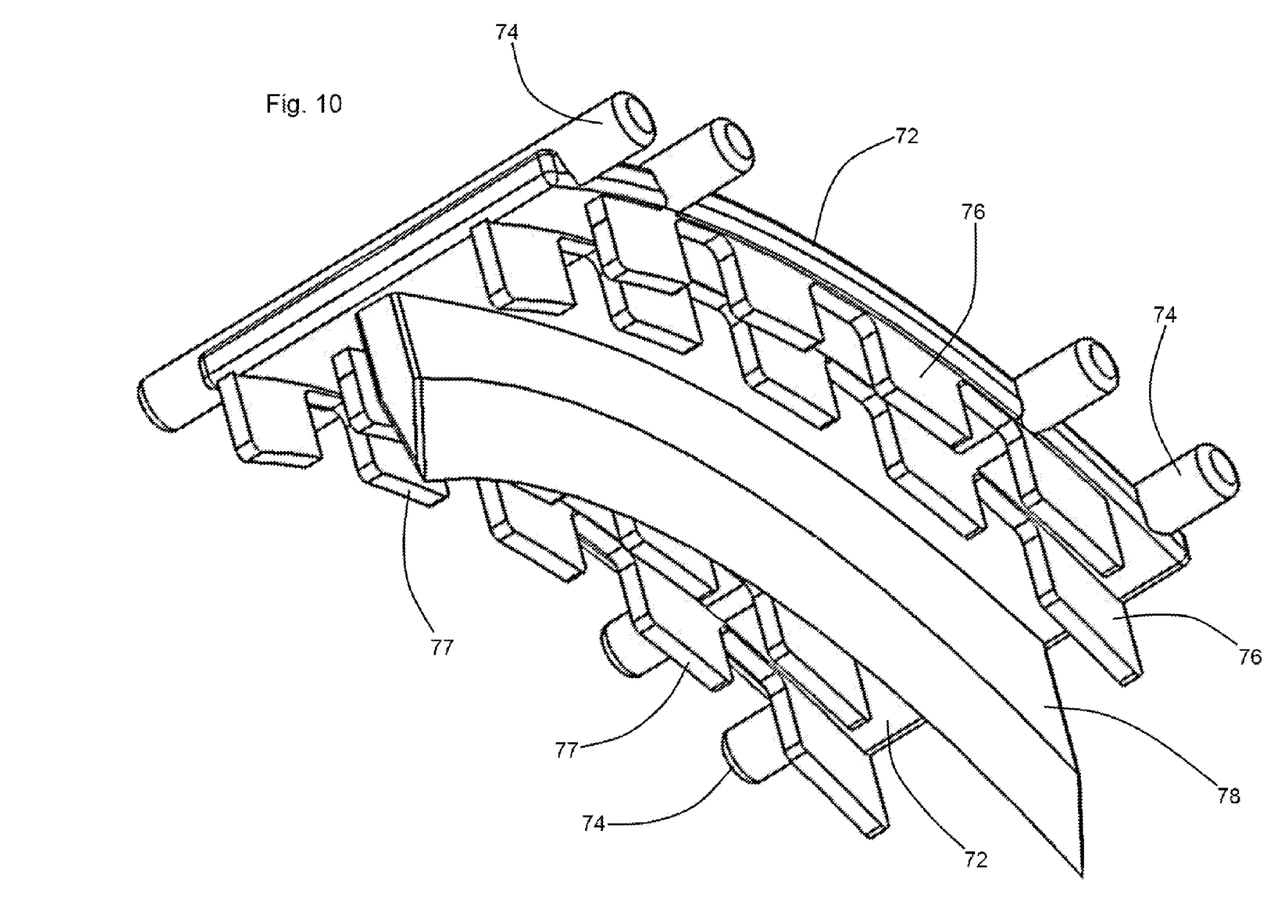
FIG. 10 is a perspective view of wholly formed blade and movable mounting means components of the inventive tool.

Referring simultaneously to FIGS. 2 and 10, front, rear and medial blades, 76, 77, and 78 are preferably provided. The inward end of the medial blade 78 preferably has an arcuate skin cutting edge, while the inner ends of the front and rear blades 76 and 77 are preferably flattened to create contact surfaces for effective skin fastener driving.

Referring further simultaneously to FIGS. 2 and 10, a housing 19 is preferably fixedly attached to and extends outwardly from the outer jaw 6, the housing 19 defining a hollow driver assembly mounting space 17. Movable mounting means are preferably operatively installed within space 17, such means preferably being adapted for facilitating alternative or reciprocating outward and inward movements of blades 76, 77, and 78. In a preferred embodiment, such movable mounting means comprise a rigid plate 72 to which the outer ends of blades 76, 77, and 78 are fixedly and rigidly attached. The movable mounting preferably further comprise a slide tracks and slide pins combination 21 and 74, the slide pins 74 extending frontwardly and rearwardly from the movable mounting means' plate 72 for engagements with preferably orthogonally aligned slide tracks 21. Springs 104, which utilize slide pins 74 as inner hooking structures, and spring hangers 20 are preferably installed for normally outwardly withdrawing plate 72 and blades 76, 77, and 78 from channels 14, 16, and 15. Such movable mounting means 20,21,72,74,104 are considered to be representative of other commonly known mechanisms and structures which are capable of facilitating reciprocating inward and outward movements of structures such as blades 76, 77, and 78 within a space such as housing space 17.

Referring simultaneously to FIGS. 1 and 2, the instant inventive circumcision tool 1 preferably further comprises driving means which are connected operatively to the front, rear, and medial blades 76, 77, and 78. In the preferred embodiment, such driving means comprise a cam 100 which is rotatably or pivotally mounted within housing space 17 by means of a longitudinally extending axle 102, such axle 102 being frontwardly supported by a front axle bearing 103 and being rearwardly supported by a rearward bearing (not shown within views). The movable mounting means' plate 72 additionally functions with, and as a part of, the driving means for translating impinging contact by the eccentric end of cam 100 into simultaneous inward motions of blades 76, 77, and 78. The axle 102 preferably extends rearwardly out of housing 19 and through hand grip 2 to rearwardly terminate at turn knob 104. The cam 100, the axle 102, and the turn knob 104 are preferably rigidly interconnected so that manually induced rotation of turn knob 104 simultaneously turns cam 100 for inward blade driving.

The cam actuated driving means depicted in FIG. 4 is considered to be representative of other commonly known mechanical driving means [such as screw actuators (not depicted within views) and such as lever actuators (also not depicted within views)] which may be suitably alternatively utilized.

Figure 6:
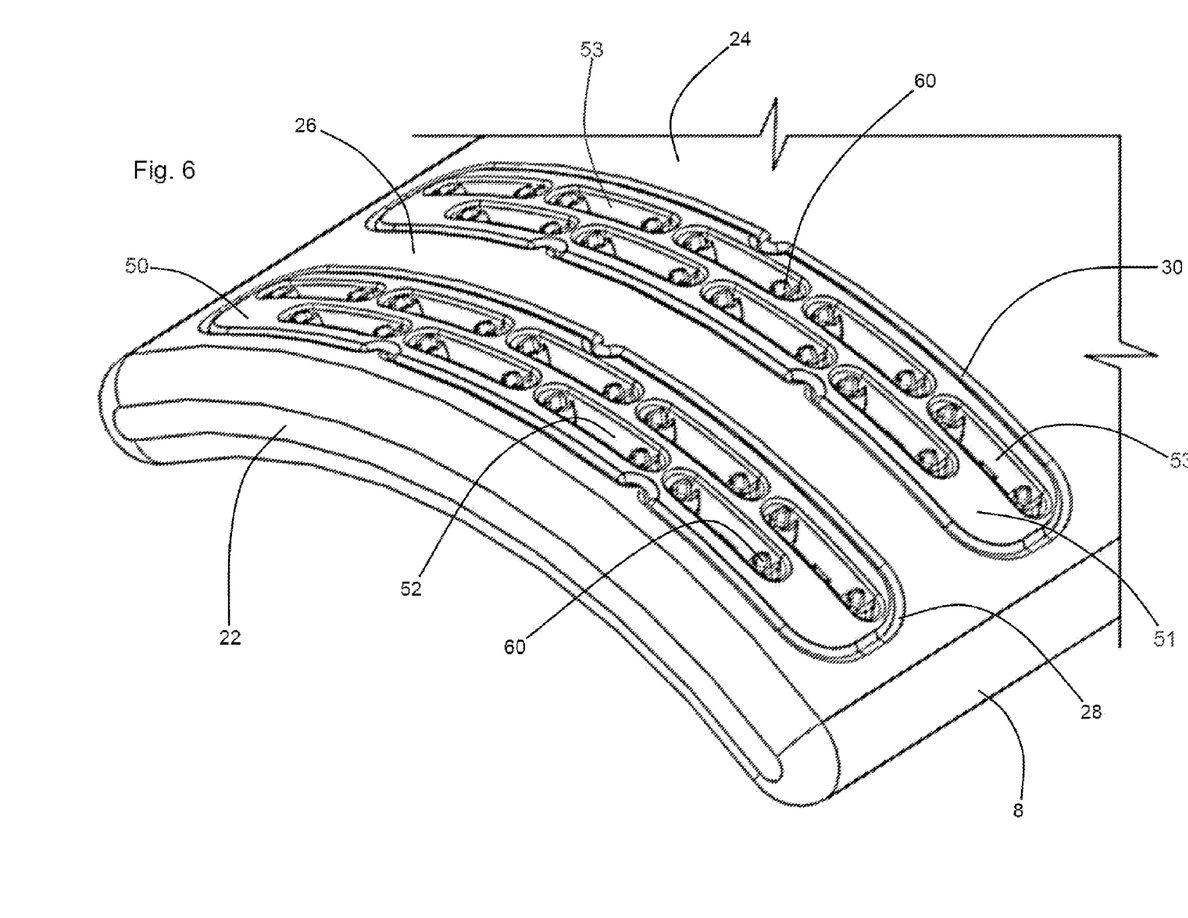
FIG. 6 is a perspective view of a forward end of a lower jaw component of the tool of FIG. 1.
Figure 7:
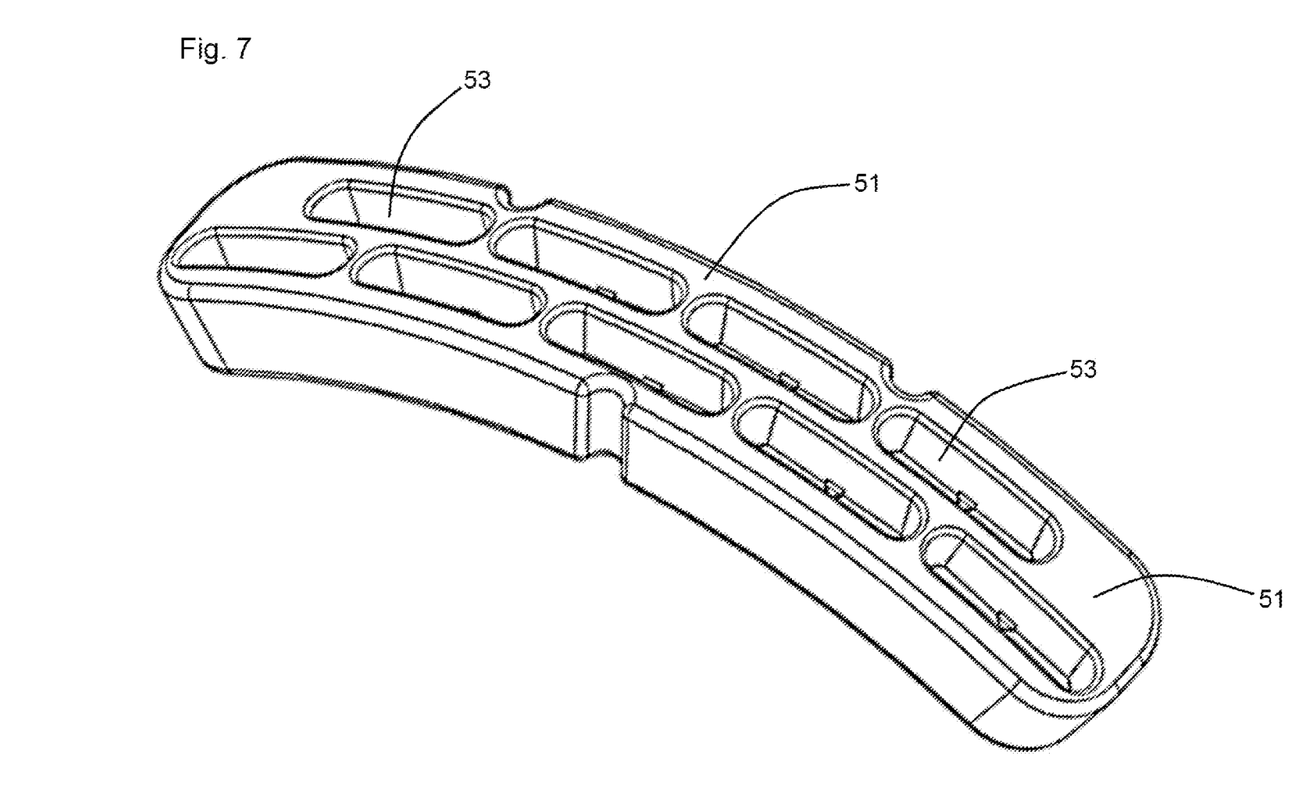
FIG. 7 is a perspective view of a rear inner insert component.
Figure 8:
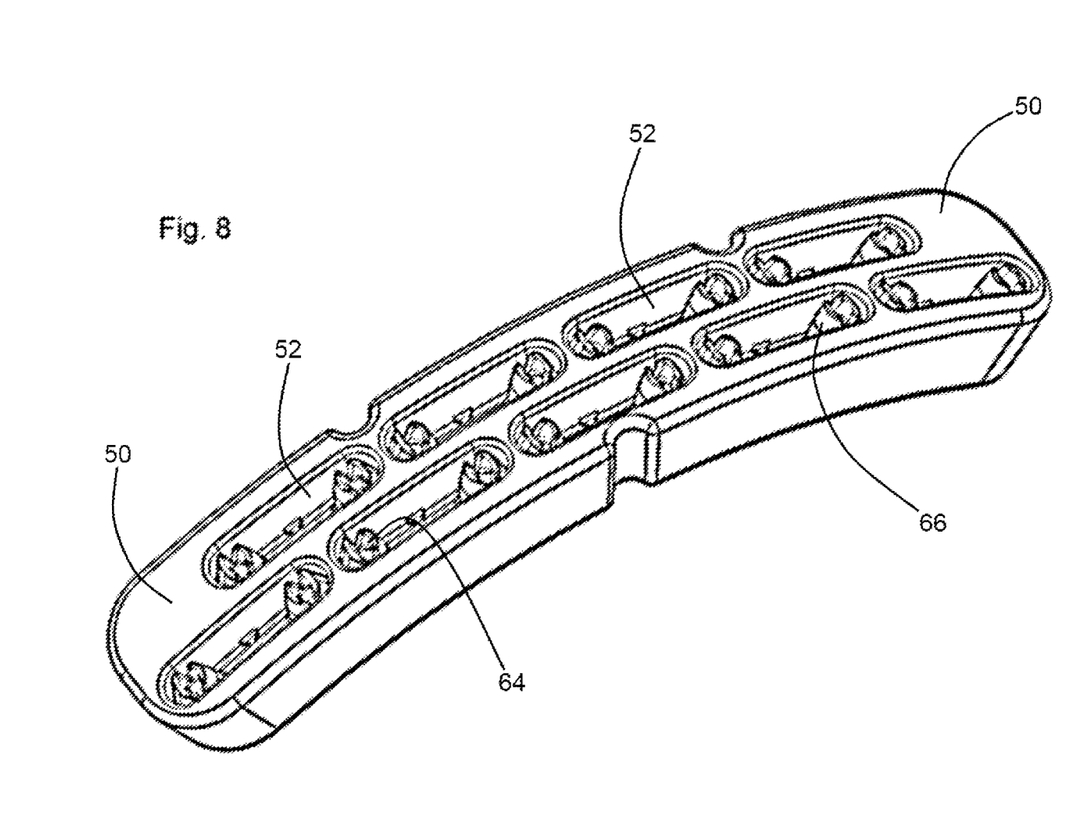
FIG. 8 is a perspective view of a front inner insert component having female staples installed.

A further structural component of the instant inventive circumcision tool comprises a lower jaw 8, which preferably has, referring simultaneously to FIGS. 2 and 6, a convex outer face 24. Referring further to FIG. 3, the curvature of the lower jaw's convex outer face 24 preferably closely matches the curvature of the outer jaw's concave inner face 12.

Referring to FIG. 1, the instant inventive circumcision tool 1 preferably further comprises clamping means which are referred to generally by Reference Arrow "C". In the preferred embodiment, the clamping means comprise a manually actuatable vice-grip assembly consisting of outer and inner hand grips 2 and 4. The forward end of hand grip 2 is preferably rigidly attached to the rearward end of the upper jaw 6, while the forward end of the inner grip 4 is pivotally attached to the inner jaw 8 at arm 11 which rigidly inwardly cantilevers from jaw 8. Jaws 6 and 8 are directly interconnected at pivot joint 9. The hand grip 4 biases against and drives the lower jaw 8 via a pivotally mounted over-center locking arm 13.

The longitudinal positioning and anchoring of the rear end of the over-center arm 13 within handle 2 is preferably selectively and adjustably controlled by turning and counter-turning of a threaded nut 5. Adjustment of nut 5 may beneficially precisely alter the extent to which the inner jaw 8 may retract toward the outer jaw 6. A site glass 7 is preferably provided to allow a medical practitioner to view the position of the base end of over-center arm 13, such viewing allowing the practitioner to precisely control the extent to which jaws 6 and 8 may retract toward each other. Such over-center arm position control advantageously allows the medical practitioner to cause the tool 1 to effectively clamp and hold a foreskin while avoiding tissue crushing. Actuation of release lever 3 beneficially trips the vice grip mechanism out of its locked over-center configuration, allowing jaws 6 and 8 to splay for foreskin release.

Referring to FIG. 6, the inner jaw 8 preferably has a rounded and curved front end 22 for easing insertions beneath a male's penile frenar band and into the foreskin opening. Front and rear channels 28 and 30 preferably open outwardly from the convex outer face 24 of the inner jaw 8, such channels 28 and 30 respectively receiving extraction stop retaining means which are preferably configured as front and rear fastener receiving inserts 50 and 51. Similarly with the outwardly overlying inserts 44 and 45, inserts 50 and 51 have slots 52 and 53 for receipts of extraction stops which, referring further to FIGS. 3-5, are preferably configured for engaging the inward skin piercing ends of outwardly positioned skin fasteners such as the male staples 32,33.

Figure 9:
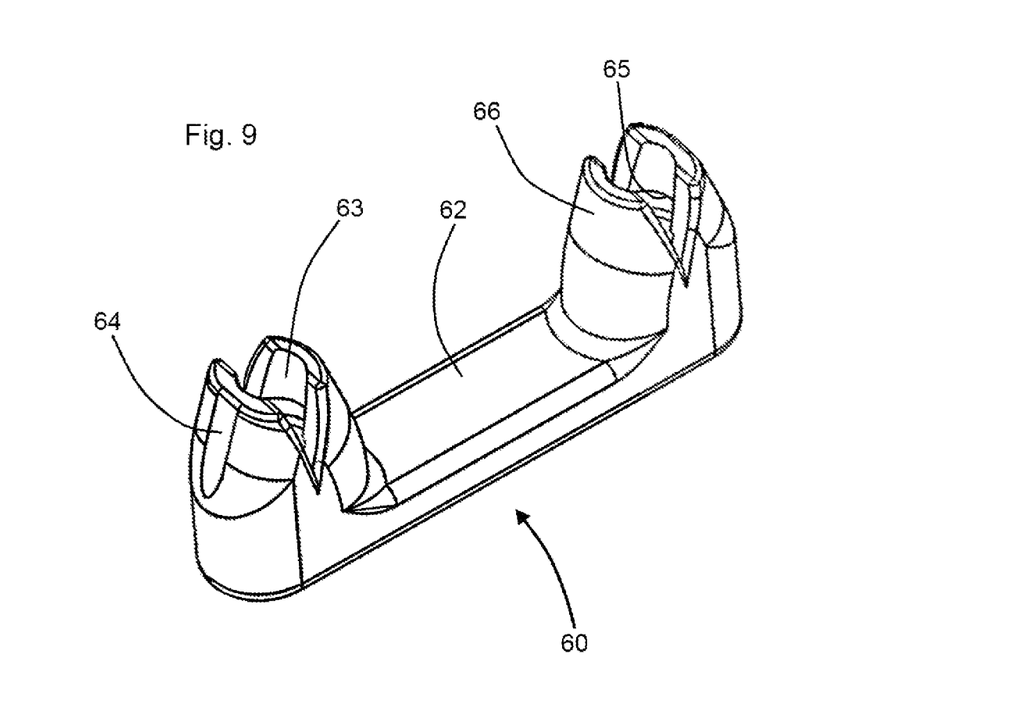
FIG. 9 is a perspective view of a female staple component of the inventive tool.

Referring simultaneously to FIGS. 6 and 9, each of the extraction stops which are mounted upon the lower jaw 8 is preferably configured as a staple 60. Each extraction stopping staple 60 is preferably configured as a "female" staple having a crown 62, and having left and right outwardly opening sockets 64 and 66. The interiors 63 of the sockets 64 and 66 preferably present downwardly facing flanges 65 which (referring further simultaneously to FIG. 5), upon inward insertions of the inward skin piercing ends 40 and 42 of the outwardly overlying "male" staples 32,33 into sockets 64 and 66, cause the inwardly facing flanges 65 to overlap and to engage outwardly facing flanges 42 and 43 for securely interconnecting the male and female staples. Accordingly, the stop attaching means preferably further comprise such inwardly facing flanges 65.

Referring to FIG. 6, extraction stop retaining means in the form of inner front and inner rear inserts 50 and 51 are preferably provided. Such inserts preferably nestingly fit within the inner front and inner rear channels 28 and 30, and the inserts preferably have slots 52 and 53 for receiving the inner front and inner rear pluralities of extraction stops 60. The channels 28 and 30 advantageously define as a part of the inner jaw face 24 an arcuately curved blade receiving and cutting land 26, such land being medially positioned between channels 28 and 30.

Referring to FIG. 1, in use of the instant inventive circumcision tool, a medical practitioner may initially grasp the tool 1 in one hand with fingers extending about inner grip 4, and may exert a slight outwardly directed pressure against grip 4, such pressure driving the rearward end of over-center arm 13 rearwardly within outer grip element 2. The rearward end of the over-center arm 13 may be viewed through site glass 7. By viewing such rearward end, the medical practitioner may manually turn and counter-turn adjustment nut 5 until the rear end of arm 13 is observed to reside at an acceptable calibrated longitudinal position. According to the function of the vice-grip clamping means "C", such calibrated longitudinal positioning of the rear end of over-center arm 13 correlates with the retraction distance between outer jaw 6 and inner jaw 8. Ideally, the medical practitioner will adjust such retraction distance to achieve a minimum jaw displacement which is slightly less than, referring further simultaneously to FIGS. 11 and 12, the combined thicknesses of the outer skin layer 79 and mucocutaneous layer 80 of the male's penile foreskin 82. Such calibrated adjustment advantageously allows for secure holding and clamping of the foreskin 82 without crushing the skin layers. Prior to or following such retraction distance calibration, referring further to FIGS. 3 and 6, outer front, outer rear, inner front, and inner rear inserts 44, 45, 50, and 51 (each being previously loaded with a plurality of skin fasteners) are inserted into the outer front, outer rear, inner front and inner rear channels 14, 16, 28, and 30.

Figure 11:
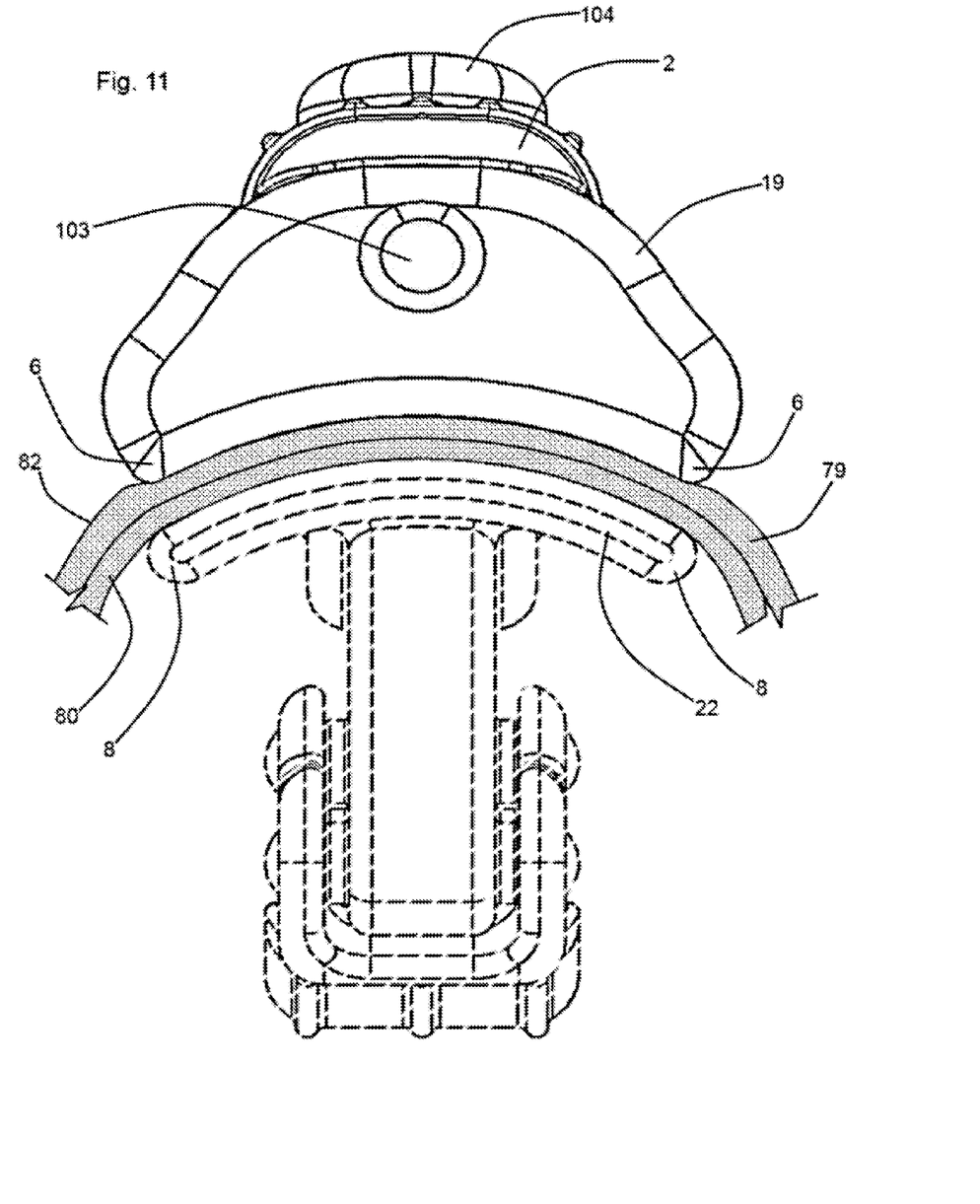
FIG. 11 is a front view of the instant inventive tool, the view showing, in accordance with the sectional view indicated in FIG. 1, clamped foreskin skin layers.
Figure 12:
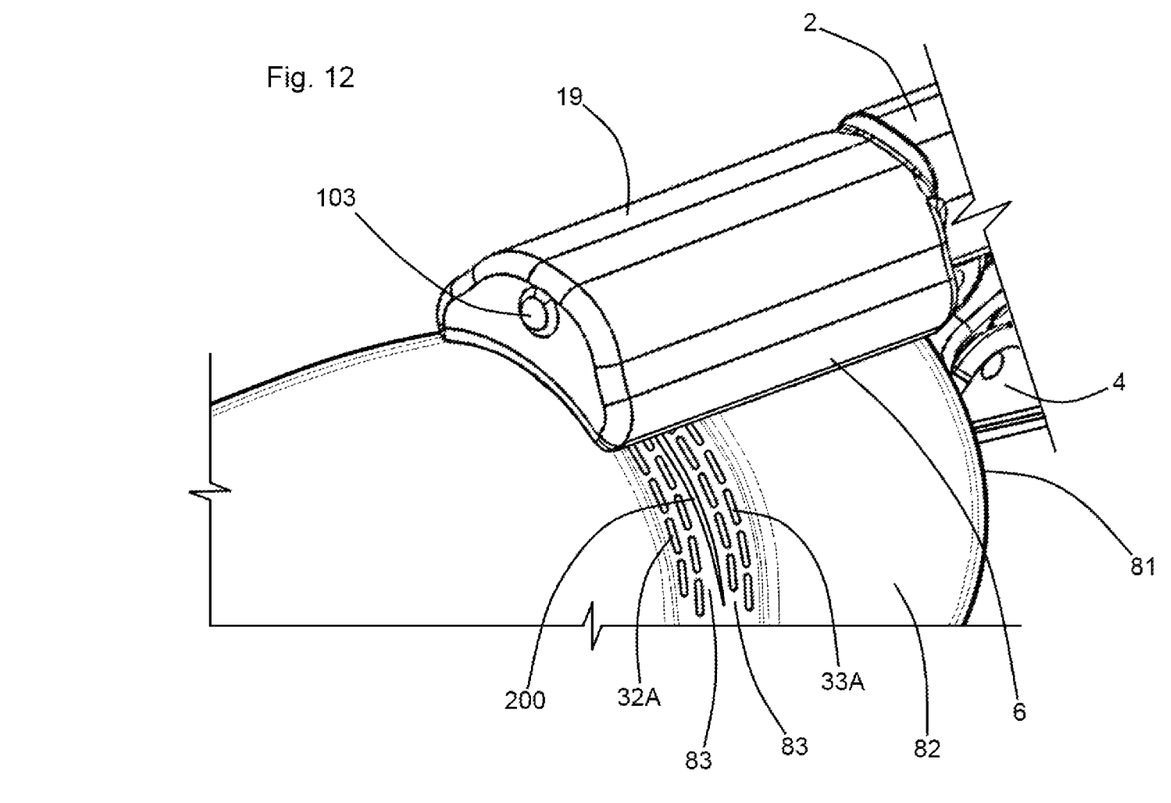
FIG. 12 is a partial perspective view of the instant inventive tool shown in use upon a male's penile foreskin.

Referring simultaneously to FIGS. 1, 11, and 12, following the clamp retraction calibration and insert loading steps discussed above, the medical practitioner may inwardly depress release lever 3, allowing jaws 6 and 8 to splay away from each other, pivoting about pivot joint 9. Thereafter, the medical practitioner may expand the frenar band 81 of the male's penile foreskin 82 to allow a forward extension of the lower jaw 8 of the circumcision tool 1 into the expanded foreskin opening, such forward extension continuing until the forward jaw end 22 reaches the proximal end of such foreskin's mucocutaneous zone, and positions the outer jaw 6 as depicted in FIG. 12. Thereafter, the medical practitioner may manually draw grip 4 outwardly toward handle 2 causing the outer face of jaw 8 to retract towards the inner face of jaw 8, and to respectively inwardly and outwardly press against the outer skin layer 79 and mucocutaneous layer 80 of the foreskin 82. Upon completion of such operation, the foreskin 82 becomes securely clamped between jaws 6 and 8.

Thereafter, referring further simultaneously to FIGS. 1, 2, 11, and 12, the medical practitioner may manually rotate turn knob 104 clockwise causing the eccentric end of cam 100 to impinge against plate 72, and causing the plate 72 along with attached blades 76, 77, and 78 to travel inwardly, such motion being tracked by the sliding motions of pins 74 within slide tracks 21.

Referring simultaneously to FIGS. 1-3, 11, and 12 such rotation of cam 100 effectively drives the front blades 76 inwardly toward front channel 14, while driving rear blades 77 toward rear channel 16, and while driving the medial cutting blade 78 inwardly toward the medial channel 15. Continued driving force applied by cam 100 to plate 72 further moves blades 76 and 77 inwardly through slots 46 and 47 within outer front and outer rear inserts 44 and 45, and further inwardly extends the cutting blade 78 through the medial channel 15. Such continued inward blade driving causes the inner ends of blades 76 and 77 to inwardly impinge against the outward crowns among the front and rear male staple arrays 32 and 33, driving such staple arrays inwardly toward the outer skin layer 79 of foreskin 82. Substantially simultaneously, such driving action causes the inner cutting edge of blade 78 to impinge against and cleave the outer skin layer 79. Continuation of such driving action causes the skin piercing ends of the male staples 32 and 33 to lance completely through the foreskin 82 and to enter the upwardly opening extraction stop attaching sockets 64 and 66 of the arrays of female staples residing within slots 52 and 53 of the inner stop retaining inserts 50 and 51. Such driving action preferably continues until, referring further simultaneously to FIGS. 5 and 9, flanges 41 and 43 of the arrays of male staples 32 and 33 engage and lock against the oppositely facing flanges 65 of the arrays of female staples 60. Upon such locking engagements, the female staples 60 effectively function as extraction stops which prevent the outwardly overlying male staples from extracting or withdrawing from the foreskin 82. The preferred female staple configured extraction stops are representative of other mechanically suitable extraction stopping means such as crimped staple legs (not depicted within views) and apertured retainer strips (also not depicted within views).

As can be seen in FIG. 12, parallel arrays 32A and 33A of staples frontwardly and rearwardly border incision 200, and such arrays advantageously define a bloodless incision zone 83. The substantially simultaneously created incision 200 which extends circumferentially within zone 83 beneficially experiences little or no hemorrhaging.

Repeated circumferentially progressing applications of the tool 1 to the foreskin 82 in the manner described above completely, substantially automatically, and substantially bloodlessly circumcises the penile foreskin 82. Alternatively, a plurality of renditions of the circumcision tool 1 may be provided, the tools of such plurality being utilized in quick succession about the foreskin 82 to complete the circumcision. Where such tools' jaw faces span 60° of arc, six of such tools may be utilized in quick succession. Utilization of such tool plurality may beneficially eliminate interruptions of the surgical procedure for staple re-loading.

The staples 32, 33, and 60 are preferably composed of a bio-absorbable polymer material which is rated to absorb and degrade at a rate slightly slower than common rates of healing, such materials choice advantageously eliminating subsequent staple removal procedures.

While the principles of the invention have been made clear in the above illustrative embodiment, those skilled in the art may make modifications in the structure, arrangement, portions, components, and method and usage steps of the invention without departing from those principles. Accordingly, it is intended that the description and drawings be interpreted as illustrative and not in the limiting sense, and that the invention be given a scope commensurate with the appended claims.

I claim:

1. A tool for interposing a circumferentially extending incision about a male's penile foreskin, the tool comprising:
    (a) an outer jaw having a length extending along a longitudinal axis, and having front, rear, and medial blade passage channels;
    (b) front and rear pluralities of skin fasteners;
    (c) outer front and outer rear retaining means respectively releasably holding the front and rear pluralities of skin fasteners within the front and rear blade passage channels;
    (d) front, rear, and medial blades, the medial blade having a circumferentially extending foreskin cutting edge;
    (e) movable mounting means connecting the front, rear, and medial blades to the outer jaw, the movable mounting means aligning said blades with planes substantially perpendicular to the outer jaw's longitudinal axis;
    (f) driving means connected operatively to the front, rear, and medial blades, the driving means being adapted for inwardly moving the front, rear, and medial blades respectively toward the front, rear, and medial blade passage channels in alignments with the front and rear pluralities of skin fasteners, and in alignment with the medial blade passage channel;
    (g) an inner jaw; and
    (h) clamping means connected operatively to the inner and outer jaws, the clamping means comprising a handle and being adapted for alternatively retracting and splaying the inner and outer jaws.

2. The tool of claim 1 wherein the outer jaw has a curved inner face, the front, rear, and medial blade passage channels opening inwardly at the curved inner face.

3. The tool of claim 2 wherein each skin fastener comprises a staple.

4. The tool of claim 3 wherein each staple is bio-absorbable.

5. The tool of claim 2 wherein the outer front and outer rear retaining means respectively comprise an outer front channel insert and an outer rear channel insert, each insert among the outer front and outer rear channel inserts having a plurality of fastener retaining slots.

6. The tool of claim 5 wherein the movable mounting means comprise a plate, the front, rear, and medial blades being fixedly attached to and extending inwardly from the plate.

7. The tool of claim 6 wherein the driving means comprise a rotatable cam operatively impinging against the plate.

8. The tool of claim 7 wherein the clamping means comprise a vice grip assembly.

9. The tool of claim 8 further comprising a driver housing fixedly attached to and extending outwardly from the outer jaw.

10. The tool of claim 1 wherein each fastener among the front and rear pluralities of skin fasteners has a skin piercing inner end, and further comprising:
    (a) a plurality of extraction stops;
    (b) stop attaching means connected operatively to the plurality of extraction stops, the stop attaching means being adapted for receiving and holding the skin fasteners' skin piercing inner ends; and
    (c) stop retaining means interconnecting the plurality of extension stops and the inner jaw, the stop retaining means positioning the extraction stops inwardly from the front and rear blade passage channels.

11. The tool of claim 10 wherein the stop attaching means comprise a plurality of outwardly opening sockets, each outwardly opening socket being fitted for receiving one of the skin fasteners' skin piercing inner ends.

12. The tool of claim 11 wherein each skin fastener among the front and rear pluralities of skin fasteners comprises a male staple, and wherein each extraction stop among the plurality of extraction stops comprises a female staple.

13. The tool of claim 12 wherein the male and female staples are bio-absorbable.

14. The tool of claim 11 wherein the stop retaining means comprise inner front and inner rear channels, each channel among the inner front and inner rear channels opening outwardly.

15. The tool of claim 14 wherein the stop retaining means further comprise an inner front slotted insert and an inner rear slotted insert, the inner front and inner rear slotted inserts being respectively fitted for nesting receipts within the inner front and inner rear channels.

16. The tool of claim 1 wherein the outer and inner jaws respectively have inner and outer foreskin compressing faces, the inner foreskin compressing face being concave and the outer foreskin compressing face being convex.

17. The tool of claim 16 wherein each blade among the front, rear, and medial blades has an inner end, and wherein the driving means are adapted for respectively and substantially simultaneously impinging the front blades' inner end against the front plurality of skin fasteners, impinging the rear blades' inner end against the rear plurality of skin fasteners, and projecting the medial blade's inner end inwardly from the medial blade passage channel for circumcising cutting.

* * * * *